United States Patent [19]

Ship

[11] Patent Number: 4,955,897
[45] Date of Patent: Sep. 11, 1990

[54] TISSUE FORCEPS

[76] Inventor: Arthur G. Ship, 9 West Dr., Larchmont, N.Y. 10538

[21] Appl. No.: 234,724

[22] Filed: Aug. 22, 1988

[51] Int. Cl.$^5$ .............................................. A61B 17/28
[52] U.S. Cl. ..................................... 606/210; 254/992; 606/207
[58] Field of Search ............... 128/321, 346, 354, 356; 294/99.2; 81/418, 419, 424.5; 433/139; D24/27; D28/55; 606/205–208, 210, 106, 211

[56] References Cited

U.S. PATENT DOCUMENTS

| | | |
|---|---|---|
| 1,949,452 | 3/1934 | Chadwick ......................... 81/424.5 |
| 2,478,595 | 8/1949 | Richter . |
| 2,504,202 | 4/1950 | Kadavy ............................. 128/354 |
| 3,140,715 | 7/1964 | Whitton, Jr. et al. . |
| 3,489,151 | 1/1970 | Eller . |
| 3,581,745 | 6/1971 | Eller . |
| 3,815,607 | 6/1974 | Chester . |
| 3,815,609 | 6/1974 | Chester ............................. 128/321 |
| 3,980,086 | 9/1976 | Kletschka . |
| 4,509,517 | 4/1985 | Zibelin . |

OTHER PUBLICATIONS

Robert A. Fischl, "A New Forceps Designed for Minimum Instrumental Trauma", from British Journal of Plastic Surgery (submitted for publication Mar., 1964), pp. 338–340.

Samuel L. Perlman, "Perforation of Adson-Type Forceps", from Plastic and Reconstructive Surgery, vol. 76, No. 6, Dec., 1985, pp. 970–971.

*Primary Examiner*—Michael H. Thaler
*Assistant Examiner*—William Lewis
*Attorney, Agent, or Firm*—Blum Kaplan

[57] ABSTRACT

Tissue forceps for grasping tissue includes a first arm having first and second ends and a second arm having first and second ends. The first end of the first and second arms are coupled together. The second ends of the first and second arms form opposing first and second jaws which are resiliently biased apart. The first and second jaws each include a plurality of sharp, directly opposing teeth which penetrate into the tissue during use when tissue is captured between the first and second jaws.

8 Claims, 2 Drawing Sheets

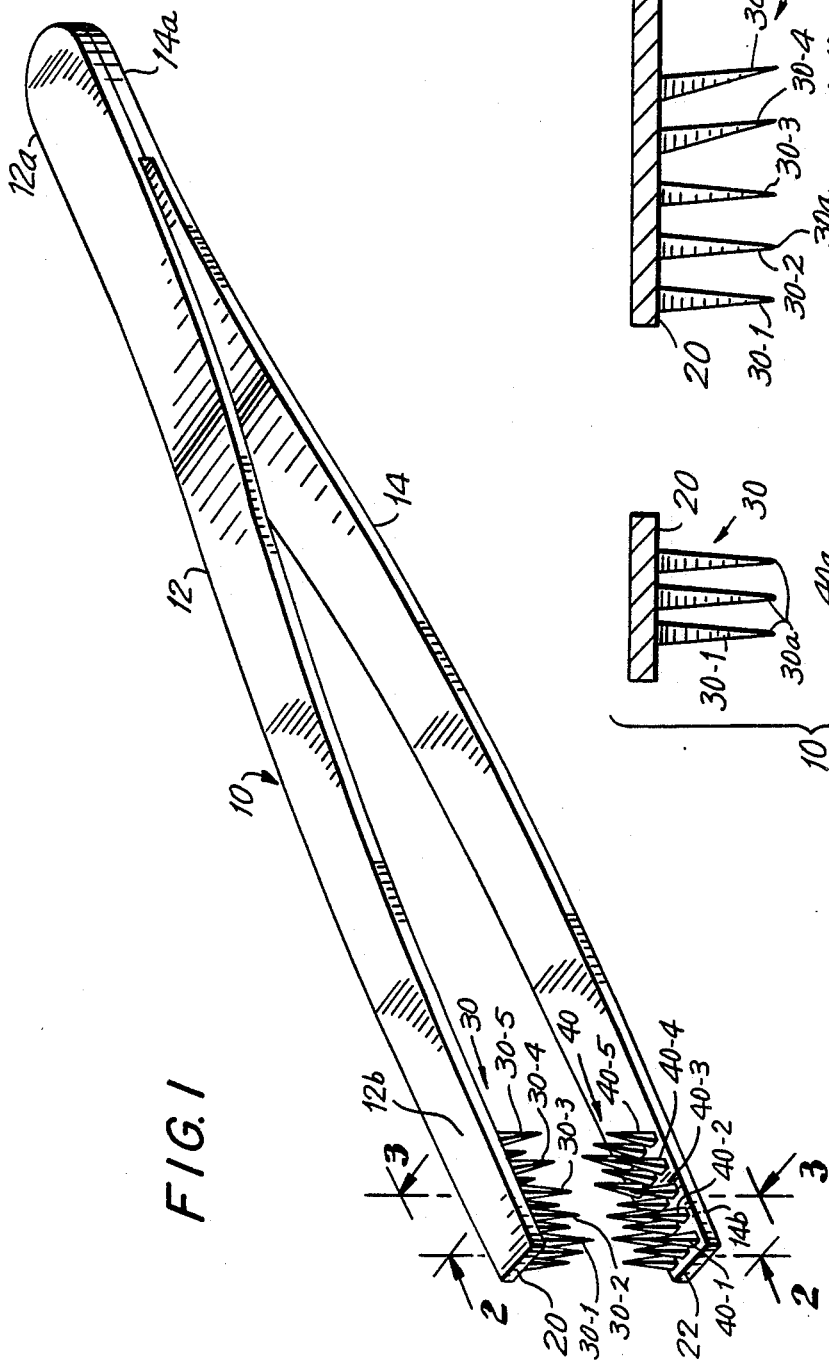
FIG.1
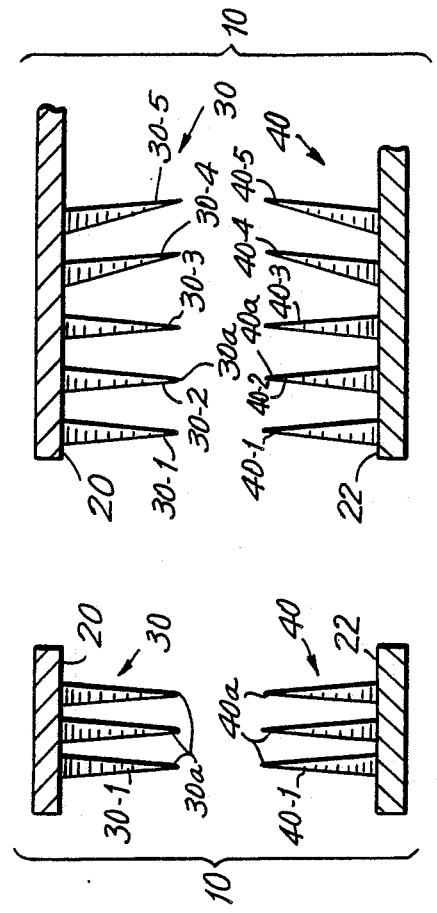
FIG.2
FIG.3

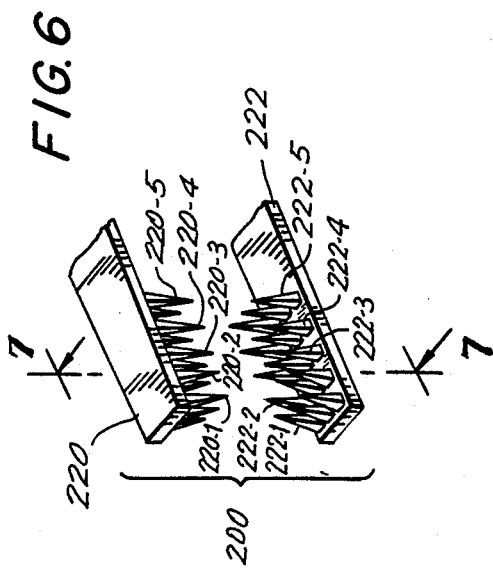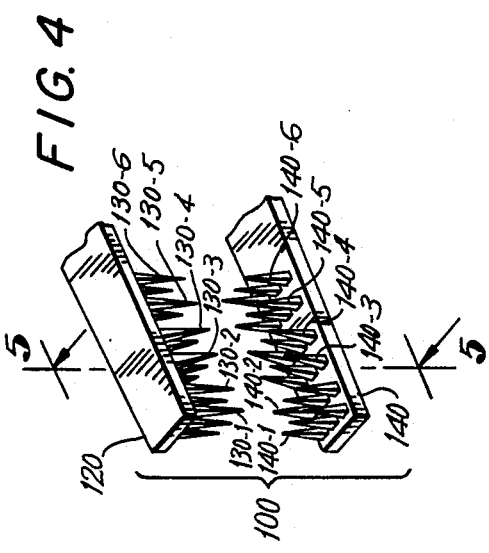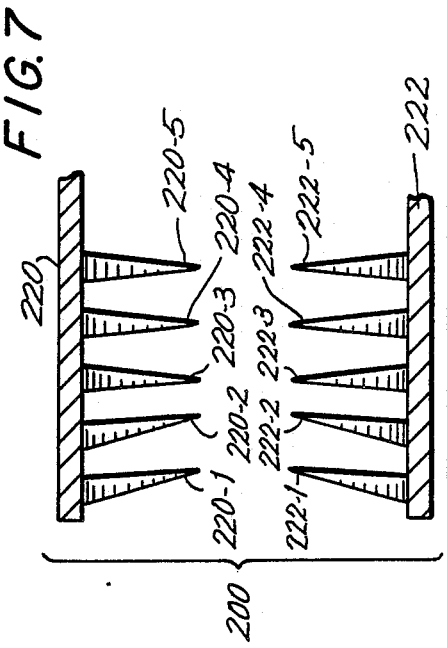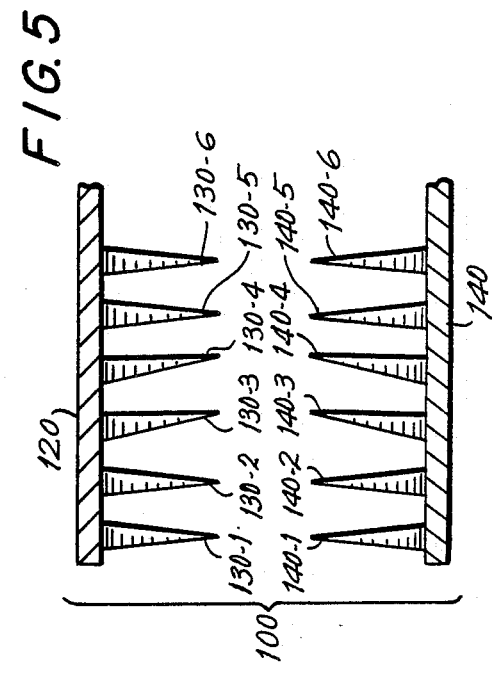

4,955,897

TISSUE FORCEPS

BACKGROUND OF THE INVENTION

The present invention is directed generally to tissue forceps and, in particular, to tissue forceps for grasping tissue which do not squeeze or crush soft tissue such as skin during use.

Forceps are used by doctors and other practitioners to grasp tissue such as skin during surgery or other medical procedures. Traditionally, forceps have been available in a number of different designs. Conventional forceps have grasping jaws at the end thereof which can be plain or smooth, finely serrated so that they will not slip during grasping, or with interdigitating teeth. One example of forceps utilizing interdigitating teeth on the opposing jaws incorporates a "mouse tooth" design utilizing one sharp triangular tooth on one jaw which is positioned intermediate two sharp triangular teeth on the second opposing jaw. When such conventional forceps are utilized on tissue such as skin, they cause a crushing injury to the skin which is often reflected in compromised healing of the wound.

The most popular forceps design used by plastic surgeons is the Adson-Brown forceps, with various modifications thereof. These forceps utilize opposing linear rows of fine teeth on each jaw of the forceps. In practice, such construction causes less trauma to tissue than the simple mouse tooth forceps or plain forceps with serrations. However, such forceps also cause a considerable amount of crushing of tissues, leaving behind visible marks on the tissue.

Accordingly, it is desired to provide an improved tissue forceps which avoids crushing of tissue during use.

SUMMARY OF THE INVENTION

Generally speaking, in accordance with the present invention, tissue forceps for grasping tissue such as skin during surgery or the like are provided. The tissue forceps include first and second arms which form the handles of the device each having first and second ends. The first end of the first and second arms are coupled together. The second ends of the first and second arms form opposing first and second jaws which are resiliently biased apart. The first and second jaws each include a plurality of sharp, directly opposing teeth which penetrate into tissue during use when the tissue is captured between the first and second jaws.

In a preferred embodiment, some of the teeth are angled inwardly to increase the effectiveness of the forceps while continuing to prevent tissue crushing.

Accordingly, it is an object of the present invention to provide an improved tissue forceps.

Another object of the present invention is to provide tissue forceps with sharp opposing teeth which penetrate tissue such as skin while avoiding crushing of tissue.

A further object of the present invention is to provide improved tissue forceps utilizing opposing sharp teeth which increase the holding power of the forceps without compromising the ability to avoid tissue damage or "rake" to provide counter-traction against the needle while sewing skin.

Yet another object of the present invention is to provide a tissue forceps which can also be used as a hook.

Still other objects and advantages of the invention will in part be obvious and will in part be apparent from the specification.

The invention accordingly comprises an article of manufacture possessing the features, properties, and the relation of elements which will be exemplified in the articles hereinafter described, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of a tissue forceps constructed in accordance with a first embodiment of the present invention;

FIG. 2 is an enlarged sectional view of the jaws taken along line 2—2 of FIG. 1;

FIG. 3 is an enlarged sectional view of the jaws taken along line 3—3 of FIG. 1;

FIG. 4 is a partial perspective view of the jaws of a tissue forceps constructed in accordance with a second embodiment of the present invention;

FIG. 5 is an enlarged sectional view of the jaws taken along line 5—5 of FIG. 4;

FIG. 6 is a partial perspective view showing the jaws of a tissue forceps constructed in accordance with a third embodiment of the present invention; and FIG. 7 is an enlarged sectional view of the jaws taken along line 7—7 of FIG. 6.

DETAILED DESCRIPTION OF THE PREFERRED EMBODIMENTS

Reference is first made to FIGS. 1 through 3 of the drawings which depict a tissue forceps, generally indicated at 10, and constructed in accordance with a first embodiment of the present invention. Tissue forceps 10 include a first arm 12 having first end 12a and second end 12b, and second arm 14 having a first end 14a and a second end 14b. Arms 12 and 14 form the handles of the forceps which may be contoured or otherwise formed to permit easy grasping between the thumb and forefinger of a user.

First end 12a of first arm 12 and first end 14a of second arm 14 are joined together in conventional fashion such as through welding or the like. It is also noted that first end 12a can be formed integrally with first end 14a to form the forceps. Second ends 12b and 14b of first and second arms 12 and 14 define opposing jaws 20 and 22 which are normally spaced apart as depicted due to the resiliency of the metal or other conventional material forming arms 12 and 14.

Jaws 20 and 22 each include a plurality of elongated, sharp teeth generally indicated at 30 and 40, respectively, formed in rows on the opposing jaws. As depicted, there are five rows of teeth in three columns. As shown in FIGS. 2 and 3, the teeth 30 are directly opposed to and facing teeth 40 so that their sharp points 30a and 40a will meet when arm 12 and arm 14 are brought towards one another through appropriate finger pressure by the user.

The teeth are generally pyramidal in shape and triangular in front elevation, each terminating in a point 30a, 40a which is adapted to pierce the tissue during use. By piercing the tissue, the teeth will dig in and penetrate the skin or tissue and avoid crushing of the tissue during use. In a preferred embodiment, the height of each tooth is four to six times the width of the base of each tooth.

As depicted in FIG. 1, the first three rows of teeth on each jaw, 30-1, 30-2 and 30-3 and 40-1, 40-2 and 40-3 extend straight out from the jaws, i.e., at 90° to the jaws. The last or inner two rows of teeth on each jaw, 30-4 and 30-5, and 40-4 and 40-5 are angled from such prependicular line to inwardly from a line perpendicular to the jaws at an angle of about 16° increase the holding power of the device.

FIGS. 4 and 5 depict an alternate embodiment of a tissue forceps 100 having jaws 120 and 140. In forceps 100, there are six rows of teeth 130-1 through 130-6 on jaw 130 and six rows of opposing teeth 140-1 through 140-6 on jaw 140. The middle two rows of teeth 130-3, 130-4 and 140-3, 140-4 instead of the last two rows of teeth are angled inwardly. Similarly, FIGS. 6 and 7 depicted that the outer two rows of teeth 220-1, 220-2 and 222-1, 222-2 at the end of jaws 220 and 222 in forceps 200 can be angled inwardly. When the outer two rows of teeth are angled inwardly as depicted in FIGS. 6 and 7, forceps 200 can also act as a hook for grabbing and pulling tissue as if they were a regular hook-type forceps.

The present invention provides an improved tissue forceps which includes jaws with opposing sharp teeth which penetrate skin or other tissue during use while preventing crushing and marking of the tissue. The forceps provide distinct advantages over conventional forceps constructions and achieve each of the advantages and benefits noted above with respect to the present invention.

It will thus be seen that the objects set forth above, among those made apparent from the preceding description, are efficiently attained, and since certain changes may be made in the above articles without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. Tissue forceps for grasping tissue, comprising a first arm having first and second ends and a second arm having first and second ends, said first end of said first and second arms being coupled together, said second ends of said first and second arms forming opposing first and second jaws which are resiliently biased apart, said first and second jaws each including a plurality of sharp, elongated teeth, each tooth on said first jaw directly opposing a tooth on said second jaw, some of said teeth extending perpendicularly from said jaws and other of said teeth extending at an acute angle from said jaws, said teeth penetrating into the tissue during use when tissue is captured between said first and second jaws by manual movement of said first jaw towards said second jaw.

2. The tissue forceps as claimed in claim 1, wherein each said tooth is pyramidal in shape and triangular in cross-section and terminates in a sharp point.

3. The tissue forceps as claimed in claim 2, wherein there are at least five rows of teeth and three columns of opposing teeth on said first and second jaws.

4. The tissue forceps as claimed in claim 3, wherein said rows of teeth include outer rows of teeth on the outer end of said first and second jaws, said angled teeth being formed on the outer two rows of teeth on said first and second rows.

5. The tissue forceps as claimed in claim 3, where said rows of teeth include inner rows of teeth on the inner end of said first and second jaws, said angled teeth being formed on the inner two rows of teeth on said first and second jaws.

6. The tissue forceps as claimed in claim 2, wherein each said tooth on said first and second jaws has a base adjacent said respective jaw on which it is located, the height of each tooth being about four to six times the width of the base of each tooth.

7. The tissue forceps as claimed in claim 1, wherein each tooth on said first jaw meets a respective tooth on said second jaw when said teeth are brought together by squeezing said arms.

8. The tissue forceps as claimed in claim 4, wherein at least some opposing teeth on said first and second jaws extend at an acute angle to a line extending perpendicularly from said respective jaws, the angle of said angled teeth to said line being about 16°.

* * * * *